US006734207B2

(12) United States Patent
Uckun et al.

(10) Patent No.: US 6,734,207 B2
(45) Date of Patent: May 11, 2004

(54) CYTOTOXIC COMPOUNDS

(75) Inventors: Fatih M. Uckun, White Bear Lake, MN (US); Shyi-Tai M. Jan, Roseville, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 10/125,746

(22) Filed: Apr. 18, 2002

(65) Prior Publication Data

US 2003/0055100 A1 Mar. 20, 2003

Related U.S. Application Data

(60) Provisional application No. 60/285,215, filed on Apr. 20, 2001.

(51) Int. Cl.[7] .................. A61K 31/38; C07D 333/32
(52) U.S. Cl. .................. 514/445; 514/448; 549/62; 549/65; 549/66; 549/70; 549/71
(58) Field of Search .................. 549/66, 70, 62, 549/65, 74, 75, 76, 78; 514/445, 448, 438

(56) References Cited

U.S. PATENT DOCUMENTS

| 4,886,885 | A | * | 12/1989 | Baker et al. .................. 514/381 |
| 4,895,869 | A | * | 1/1990 | Djuric et al. .................. 514/438 |
| 5,217,981 | A | * | 6/1993 | Djuric et al. .................. 514/340 |
| 5,591,756 | A | * | 1/1997 | Djuric et al. .................. 514/350 |
| 6,258,841 | B1 | | 7/2001 | Uckun et al. |

FOREIGN PATENT DOCUMENTS

| EP | 0 491 956 A1 | 6/1990 |
| JP | 05117169 | 5/1993 |
| WO | WO 92/18465 | 10/1992 |
| WO | WO 99/36414 | 7/1999 |
| WO | WO 00/00469 | 1/2000 |

OTHER PUBLICATIONS

De Sousa et al, CA114:206919, 1996.*
Avila, J., *Life Sci.*, 50, 327–334 (1992) "Microtubule Functions".
Bacon, D. et al., *J. Molec. Graphics*, 6(4), 219–220 (1988) "A Fast Algorithm for Rendering Space–Filling Molecule Pictures".
Bai, R. et al., (Oct. 1993), *Molecular Pharmacology*, 44(4):757766 "Spongistatin 1, a Highly Cytotoxic, Sponge–Derived, Marine Natural Product that Inhibits Mitosis, Microtubule Assembly, and the Binding of Vinblastine to Tubulin".
Böhm, H., *J. Comput. Aided.. Mol. Des.*, 6, 593–606 (1992) "LUDI: rule–based automatic design of new substituents for enzyme inhibitor leads".
Böhm, H., *J. Comput. Aided.. Mol. Des.*, 8(3), 243–256 (1994) "The development of a simple empirical scoring function to estimate the binding constant for a protein–ligand complex of known three–dimensional structure".

Carlson, D. et al., "Dimethyl Disulfide Derivatives of Long Chain Alkenes, Alkadienes, and Alkatrienes for Gas Chromatography/Mass Spectrometry", *Anal. Chem*, vol. 61, No. 14, pp. 1564–1571 (1989).
Chen, Y. et al., "Tonkinecin, A Novel Bioactive Annonaceous Acetogenin from *Uvaria tonkinesis*",*J. Nat. Prod.*, vol. 59, No. 5, pp. 507–509 (1996).
Chen, Y. et al., "Solubilization, Partial Purification, and Affinity Labeling of the Membrane–Bound Isoprenylated Protein Endoprotease", *Biochemistry*, vol. 35, No. 10, pp. 3227–3237 (1996).
Cohen, T. et al., (Mar. 2, 1990), *J. Org. Chem.*, 55(5):1528–1536 "Synthetically Useful ϱ–Lithioalkoxides from Reductive Lithiation of Epoxides by Aromatic Radical Anions".
Colman–Saizarbitoria, T. et al., "Venezenin: A New Bioactive Annonaceous Acetogenin From the Bark of *Xylopia Aromatica*", *J. Nat. Prod.* vol. 58, No. 4, pp. 532–539 (Apr. 1995).
Connolly, M., *Science*, 221(4612), 709–713 (1983) "Solvent–Accessible Surface of Proteins and Nucleic Acids".
Corey, E. et al., (Aug. 23, 1972), *J. Am. Chem. Soc.*, 94(17):61906191 "Protection of Hydroxyl Groups as tert–Butyldimethylsilyl Derivatives".
Danishefsky, S. et al., (Dec. 23, 1987), *J. Am. Chem. Soc.*, 109(26):8117–8119 "The Total Synthesis of the Aglycon of Avermectin $A_{1a}$".
Downing, K. et al., *Curr. Opin. Cell Biol*, 10, 16–22(Feb. 1998) "Tubulin and microtubule structure".
Evans, D. et al., "Enantioselective Synthesis of Altohyrtin C (Spongistatin 2): Fragment Assembly and Revision of the Spongistatin 2 Stereochemical Assignment", *Angew Chem. Int. Ed. Engl.*, vol. 36, No. 24, pp. 2744–2747 (1997).
Evans, D. et al., "Enantioselective Synthesis of Altohyrtin C (Spongistatin 2): Synthesis of the AB– and CD–Spiroketal Subunits", *Angew Chem. Int. Ed. Engl.*, vol. 36, No. 24, pp. 2738–2741 (1997).
Smith, III, A. et al., "Spongistatin Synthetic Studies. 2. Assembly of the C(18–28) Spiroketal", *Tetrahedron Letters*, vol. 38, No. 50, pp. 8671–8674 (1997).
Figadere, B. et al., "Synthesis of 2,33–Dihydro4–Oxo–Murisolin: Conjugate Addition of Primary Alkyl Iodides to αβ–Unsaturated Ketones", *Tetrahedron Lett.*, vol. 33, No. 36, pp. 5189–5192 (1992).

(List continued on next page.)

*Primary Examiner*—Deborah C Lambkin
(74) *Attorney, Agent, or Firm*—Merchant & Gould P.C.

(57) ABSTRACT

Compounds are described that bind to tubulin causing tubulin depolymerization and inhibiting tubulin polymerization. The compounds of the invention are therapeutically effective to inhibit cellular proliferation, for example, as effective anti-cancer agents. The compounds can also induce cytotoxicity in cells such as leukemia cells. The chemical structure of the compounds includes a furan, thiophene, thiazole, oxazole, or imidazole group at one end of the molecule (head) and a hydrophobic, aliphatic chain at the other end of the molecule (tail).

17 Claims, No Drawings

OTHER PUBLICATIONS

Guo, J. et al., "Total Synthesis of Altohyrtin A (Spongistatin 1): Part 1", *Angew Chem. Int. Ed.*, vol. 37, No. 1/2, pp. 1871–1892 (1998).

Hyman, A. et al., *J. Cell Sci.*, 111, (Pt 15), 2077–2083 (1998) "The role of nucleation in patterning microtubule networks".

Jiang, J. et al., *Cancer Research*, 58, 5389–5395 (1998) "3–(Iodoacetamido)–benzoylurea: A Novel Cancericidal Tubulin Ligand that Inhibits Microtubule Polymerization, Phosphorylates bcl–2, and Induces Apoptosis in Tumor Cells".

Jan, S. et al., *Tetrahedron Letters*, 40, 193–196 (1999) "Stereoselective Synthesis of a Versatile Intermediate for the Total Synthesis of Mono– and Bis–THF Containing Annonaceous Acetogenins".

Kimmel, C. et al., *Dev. Dynam.*, 203(3), 253–310 (1995) "Stages of Embryonic Development of the Zebrafish".

Kozielski, F. et al., *Curr. Biol.*, 8(4), 191–198 (1998) "A model of the microtubule–kinesin complex based on electron cryomicroscopy and X–ray crystallography".

Kraulis, P., *J. Appl. Cryst.*, 24(5), 946–950 (1991) "MOLSCRIPT: a program to produce both detailed and schematic plots of protein structures".

Li, K. et al., *Tetrahedron*, 39, 2063–2066 (1998) "Sterocontrolled Synthesis of the Tetrahydrofuran Unit of Annonaceous Acetogenins".

Luty, B. et al., *J. Comp. Chem.*, 16(4), 454–464 (1995) "A Molecular Mechanics / Grid Method for Evaluation of Ligand–Receptor Interactions".

Makabe, H. et al., (1996), *Heterocycles*, 43(10):2229–2248 "Total Synthesis of (8'R)– And (8'S)– Corossoline".

Mao, C. et al., *Bioorganic & Medicinal Chemistry Letters*, 8, 2213–2218 (1998) "Structure–Based Design of N–[2–(1–Piperidinylethyl)]–N'–[2–(5–Bromopyridyl)]–Thiourea and N–[2–(1Piperazinylethyl)]–N' –[2–(5–Bromopyridyl)]–Thiourea as Potent Non–Nucleoside Inhibitors of HIV1 Reverse Transcriptase".

Merritt, E. et al., *Acta Cryst*, D50(6), 869–873 (1994) "Raster3D Version 2.0. A Program for Photorealistic Molecular Graphics".

Narla, R. et al., *Clin. Cancer Res.*, 4, 2463–2471 (1998) "Inhibition of Human Glioblastoma Cell Adhesion and Invasion by 4–(4'Hydroxylphenyl)–amino–6,7–dimethoxyquinazoline (WHI–P131) and 4–(3'–Bromo–4'–hydroxylphenyl)–amino–6,7–dimethoxyquinazoline (WHI–P154)".

Nogales, E. et al., *Nature*, 391, 199–202 (1998) "Structure of the I9 tubulin dimer by electron crystallography".

Nogales, E., (Jan. 8, 1999), *Cell*, 96(1):79–88 "High–Resolution Model of the Microtubule".

Nicholls, A. et al., (1991), *Proteins, Structure, Function and Genetics*, 11:281–296 "Protein Folding and Association: Insights From the Interfacial and Thermodynamic Properties of Hydrocarbons".

Paterson, I. et al., "Studies in Marine Macrolide Synthesis: Stereocontrolled Synthesis of the AB–Spiroacetal Subunit of Spongistatin 1 (Altohyrtin A)", *Tetrahedron Letters*, vol. 37, No. 47, pp. 8581–8584 (1996).

Paterson, I. et al., "Studies in Marine Macrolide Synthesis: Synthesis of a Fully Functionalised $C_1$–$C_{28}$ Subunit of Spongistatin 1 (Altohyrtin A)", *Tetrahedron Letters* 39, pp. 8545–8548 (1998).

Paterson, I. et al., "Studies in Marine Macrolide Synthesis: Synthesis of the $C_1$–$C_{15}$ Subunit of Spongistatin 1 (Altohyrtin A) and 15,16–Anti Aldol Coupling Reactions", *Tetrahedron Letters*, vol. 38, No. 47, pp. 8241–8244 (1997).

Paterson, I. et al., "Studies in Marine Macrolide Synthesis: Synthesis of a $C_{16}$–$C_{28}$ Subunit of Spongistatin 1 (Altohyrtin A) Incorporating the CD–Spiroacetal Moiety", *Tetrahedron Letters*, vol. 38, No. 51, pp. 8911–8914 (1997).

Schulz, S., "New Lipids From Spiders and Insects", *Chemical Abstract*, vol. 124, No. 19, 1 pg. (May 6, 1996).

Schulz, S. et al., "2,5–Dialkyltetrahydrofurans, Common Components of the Cuticular Lipids of Lepidoptera", *Z. Naturforsch C: Biosci.*, vol. 53, pp. 107–116 (1998).

Smith, III, A. et al., "Spongistatin Synthetic Studies. 3. Construction of the C(1–17) Spiroketal", *Tetrahedron Letters*, vol. 38, No. 50, pp. 8675–8678 (1997).

Smith, III, A. et al., "Spongistatin Synthetic Studies. 3. Construction of the C(18–28) Spiroketal", *Tetrahedron Letters*, vol. 38, No. 50, pp. 8671–8675 (1997).

Terauchi, T. et al., "Synthetic Studies on Altohyrtins (Spongistatins): Synthesis of the C1–C14 (AB) Spiroacetal Portion", *Tetrahedron Letters 39*, pp. 3795–3798 (1998).

Towne, T. et al., "syn–Oxidative Polycyclizations of Hydroxypolyenes: Highly Stereoselective and Potentially Biomimetic Syntheses of all–trans–Polytetrahydrofurans", *J. Am. Chem. Soc.*, vol. 119, No. 26, pp. 6022–6028 (1997).

Uckun, F. et al., *Blood*, 85(10), 2817–2828 (1995) "In Vitro and In Vivo Activity of Topotecan Against Human B–Lineage Acute Lymphoblastic Leukemia Cells".

Vassilev, A., et al., *J. Biol. Chem.*, 274(3), 1646–1656 (1999) "Bruton's Tyrosine Kinase as an Inhibitor of the Fas/CD95 Death–inducing Signaling Complex".

Vig, R. et al., *Bioorganic & Medicinal Chemistry*, 6, 1789–1797 (1998) "Rational Design and Synthesis of Phenethyl–5–bromopyridyl Thiourea Derivatives as Potent Non–nucleoside Inhibitors of HIV Reverse Transcriptase".

Vig, R. et al., *Bioorg. & Med. Chem. Lett.*, 8, 1461–1466 (1998) "5–Alkyl–2–[(Methylthiomethyl)Thio]–6–(Benzyl)– Pyrimidin–4–(1H)–Ones as Potent Non–Nucleoside Reverse Transcriptase Inhibitors of S–Dabo Series".

Woo, M. et al., "Asimilobin and CIS– and Trans–Murisolinones, Novel Bioactive Annonaceous Acetogenins From The Seeds Of *Asimina Triloba*", *J. Nat. Prod.*, vol. 58, No. 10, pp. 1533–1542 (Oct. 1995).

Wu, F. et al., "Additional Bioactive Acetogenins, Annomutacin And (2,4–Trans and CIS–)10R–Annonacin–A–Ones, From The Leaves of *Annona Muricata*", *J. Nat. Prod.*, vol. 58, No. 9, pp. 1430–1437 (Sep. 1995).

Ye, Q. et al., "Longicin and Goniothalamicinone: Novel Bioactive Monotetrahydrofuran Acetogenins from *Asimina Longifolia*", *J. Nat. Prod.*, vol. 58, No. 9, pp. 1398–1406 (Sep. 1995).

* cited by examiner

CYTOTOXIC COMPOUNDS

PRIORITY OF THE APPLICATION

This application claims priority to U.S. Provisional Application 60/285,215 filed Apr. 20, 2001.

FIELD OF THE INVENTION

The invention relates to novel compounds that are effective anti-cancer agents and potent inhibitors of tubulin polymerization.

BACKGROUND OF THE INVENTION

Cancer is a major disease that continues as one of the leading causes of death at any age. In the United States alone, it is estimated that more than a half a million Americans will die annually of cancer. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

Cellular proliferation, for example, in cancer, occurs as a result of cell division, or mitosis. Microtubules play a pivotal role in mitotic spindle assembly and cell division. These cytoskeletal elements are formed by the self-association of the αβ tubulin heterodimers.

Recently, the structure of the αβ tubulin dimer was resolved by electron crystallography of zinc-induced tubulin sheets. According to the reported atomic model, each 46×40×65 Å tubulin monomer is made up of a 205 amino acid N-terminal GTP/GDP binding domain with a Rossman fold topology typical for nucleotide-binding proteins, a 180 amino acid intermediate domain comprised of a mixed β sheet and five helices which contain the taxol binding site, and a predominantly helical C-terminal domain implicated in binding of microtubule-associated protein (MAP) and motor proteins.

As disclosed in U.S. Pat. No. 6,258,841 B1, tubulin has a binding pocket in a region within the intermediate domain of tubulin, located between the GDP/GTP binding site and the taxol binding site. The approximate dimensions of the binding pocket are 6 Å×22 Å×7 Å. The pocket, referred to as the COBRA binding pocket, has an abundance of leucine residues (7 leucine and 2 isoleucine) providing a highly hydrophobic binding environment. It is characterized by a narrow cavity with elongated dimensions, suitable for accommodating an aliphatic chain of up to about 12 carbons.

Compounds that bind with the COBRA binding pocket can interfere with tubulin polymerization and can provide novel agents for the treatment of cancer.

SUMMARY OF THE INVENTION

The compounds of the invention bind to tubulin causing tubulin depolymerization and inhibiting tubulin polymerization. The tubulin binding compounds of the invention are therapeutically effective to inhibit cellular proliferation, for example, as effective anti-cancer agents. The compounds are cytotoxic against tumor cells such as leukemia cells. The compounds are novel furan, thiophene, thiazole, oxazole, or imidazole derivatives.

One aspect of the invention includes COBRA compounds represented by the general formula I:

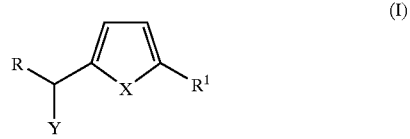

(I)

where
X is O, S, or NH;
R is a saturated or unsaturated ($C_7$ to $C_{15}$) hydrocarbon chain;
$R^1$ is hydrogen, halogen, OH, ($C_1$ to $C_6$) alkoxy, ($C_1$ to $C_6$) acyl, ($C_1$ to $C_6$) ester, or ($C_1$ to $C_6$) carboxylic acid;
Y is OH, SH, CN, halogen, or ($C_1$ to $C_6$) alkoxy; and
pharmaceutically acceptable salts thereof.

In another aspect of the invention, COBRA compounds are provided of the general formula II:

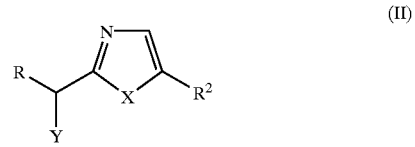

(II)

where
X is NH, O, or S;
R is a saturated or unsaturated ($C_7$ to $C_{15}$) hydrocarbon chain;
$R^2$ is hydrogen, OH, ($C_1$ to $C_6$) alkoxy, ($C_1$ to $C_6$) alkyl, ($C_1$ to $C_6$)alkenyl, ($C_1$ to $C_6$) alkynyl, ($C_3$ to $C_7$) cycloalkyl, aryl, heteroaryl, halogen, ($C_1$ to $C_6$) acyl, ($C_1$ to $C_6$) ester, or ($C_1$ to $C_6$) carboxylic acid;
Y is OH, SH, CN, halogen, or ($C_1$ to $C_6$) alkoxy; and
pharmaceutically acceptable salts thereof.

In yet another aspect of the invention, the COBRA compound has the general formula III:

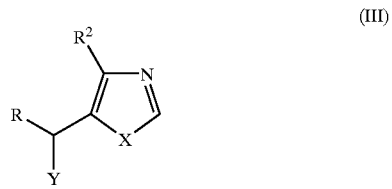

(III)

where
X is NH, O, or S;
R is a saturated or unsaturated ($C_7$ to $C_{15}$) hydrocarbon chain;
$R^2$ is hydrogen, OH, ($C_1$ to $C_6$) alkoxy, ($C_1$ to $C_6$) alkyl, ($C_1$ to $C_6$)alkenyl, ($C_1$ to $C_6$) alkynyl, ($C_3$ to $C_7$) cycloalkyl, aryl, heteroaryl, halogen, ($C_1$ to $C_6$) acyl, ($C_1$ to $C_6$) ester, or ($C_1$ to $C_6$) carboxylic acid;
Y is OH, SH, CN, halo, or ($C_1$ to $C_6$) alkoxy;
and pharmaceutically acceptable salts thereof.

DETAILED DESCRIPTION OF THE INVENTION

Definitions

All scientific and technical terms used in this application have meanings commonly used in the art unless otherwise specified. As used in this application, the following words or phrases have the meanings specified.

As used herein, "acyl" refers to a group containing a carbon attached to oxygen by a double bond. Acyl groups can be a part of, for example, aldehydes or ketones. Typically, acyl groups include 1 to 15 carbon atoms or 1 to 6 carbon atoms. The carbon atoms can be aliphatic or aromatic. In some embodiments, the acyl group has 1 to 3 carbon atoms or 1 carbon atom.

The term "alkyl" refers to straight or branched hydrocarbon radicals, such as methyl, ethyl, propyl, butyl, pentyl, octyl, isopropyl, tert-butyl, sec-butyl, and the like. Typically, alkyl groups include 1 to 15 carbon atoms, 1 to 6 carbon atoms, or 1 to 3 carbon atoms.

As used herein, "alkythio" comprises a sulfur attached to an alkyl by a single bond. Typically, alkythio groups include 1 to 15 carbon atoms, 1 to 6 carbon atoms, or 1 to 3 carbon atoms.

As used herein, "alkene" and "alkenyl", includes both branched and straight chain aliphatic hydrocarbon groups that have at least one double bond. Typically, alkene groups include 1 to 15 carbon atoms, 1 to 6 carbon atoms, or 1 to 3 carbon atoms.

The term "alkoxy" refers to an oxygen atom substituted with an alkyl radical as defined above. Typical alkoxy groups include 1 to 15 or 1 to 6 carbon atoms or 1 to 3 carbon atoms such as methoxy, ethoxy, propoxy, iso-propoxy, and the like. Preferable alkoxy groups include methoxy and ethoxy.

As used herein, "alkyne" and "alkynyl" includes both branched and straight chain aliphatic hydrocarbon groups that have at least one triple bond. Typically, alkyne groups include 1 to 15 carbon atoms, 1 to 6 carbon atoms, or 1 to 3 carbon atoms.

As used herein "amine" refers to compounds of the formula $NR^aR^b$ and includes primary, secondary, and tertiary amines. $R^a$ and $R^b$ are each independently hydrogen, ($C_1$ to $C_6$) alkyl, aryl, heteroaryl, ($C_1$ to $C_6$) acyl, ($C_3$ to $C_7$) cycloalkyl, or $R^a$ and $R^b$ taken together with the nitrogen to which they are attached form a ring such as pyrrolidino, piperidino, morpholino, or thiomorpholino.

The term "aryl" refers to monovalent unsaturated aromatic carbocyclic radicals having a single ring, such as phenyl, or multiple fused rings, such as naphthyl or anthryl.

As used herein, "aryloxy" comprises an oxygen attached to an aryl by a single bond.

As used herein, "cycloalkyl" includes cyclic alkanes having 3 to 7 carbon atoms.

As used herein, an "ester" comprises a carbon attached to a first oxygen by a double bond and to a second oxygen by a single bond. The second oxygen is also attached to an alkyl group which has 1 to 15 carbon atoms, 1 to 6 carbon atoms, or 1 to 3 carbon atoms.

As used herein, the term "carboxylic acid" comprises a carbon attached to a first oxygen by a double bond and to a second oxygen by a single bond. The second oxygen is also attached a hydrogen atom, i.e. COOH.

As used herein, the terms "halogen" or "halo" refers to fluoride, chloride, bromide, and iodide radicals.

As used herein, "heteroaryl" includes substituted or unsubstituted aromatic hydrocarbon compounds having at least one atom of O, N or S in an aromatic ring. Typical heteroaryl groups include, for example, furan, thiophene, pyrrole, thiazole, oxazole, or imidazole group. Heteroaryl groups can include two aromatic groups fused together such as, for example, benzothiophene, indole, carbazole, quinazoline, quinoline, and purine.

As used herein, the term "thioacyl" refers to a group comprising a carbon atom attached to a sulfur atom by a double bond. Typically, the thioacyl group has 1 to 6 carbon atoms or 1 to 3 carbon atoms.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

"Treating" or "Treatment" in the context of this invention means the prevention or reduction in severity of symptoms or effects of a pathological condition, including prolonging life expectancy. In the context of cancer therapy, treatment includes prevention of tumor growth, reduction of tumor size, enhanced tumor cell death, and increased apoptosis.

COBRA Binding Pocket on Tubulin

The COBRA binding pocket accommodates COBRA compounds. As used herein, the phrase "COBRA compound" refers to a compound having a non-linear polar group at one end of a molecule (the head) and a aliphatic, hydrophobic group at the other end of the molecule (the tail). The structure of the COBRA compounds increases the attraction of the compounds to the COBRA pocket and increases the residence time of the molecule in the binding pocket.

The residues of the COBRA binding pocket suitable for interaction with the tail part of COBRA compounds include Asp367, Leu217, Val275, Ile 276, Leu368, Tyr272, Ile212, Ile234, Gln233, Leu230, His229, Ile209, Ile231, and Leu23. Residues of the pocket suitable for interaction with the head part of COBRA compounds include Asn226, Pro222, and Ile219.

Compounds of the Invention

In general, the COBRA compounds of the invention include an aliphatic, hydrophobic tail part and a non-linear polar head part. The head part is a furan, thiophene, pyrrole, thiazole, oxazole, or imidazole group. The compounds are suitable for binding to the COBRA binding pocket of tubulin.

One aspect of the invention includes COBRA compounds represented by the general formula I:

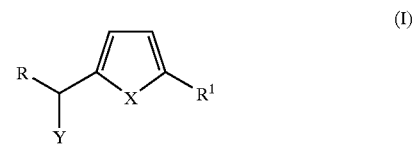

(I)

where
X is O, S, or NH;

R is a saturated or unsaturated ($C_7$ to $C_{15}$) hydrocarbon chain;

$R^1$ is hydrogen, halogen, OH, ($C_1$ to $C_6$) alkoxy, ($C_1$ to $C_6$) acyl, ($C_1$ to $C_6$) ester, or ($C_1$ to $C_6$) carboxylic acid;

Y is OH, SH, CN, halogen, or ($C_1$ to $C_6$) alkoxy; and pharmaceutically acceptable salts thereof.

The saturated or unsaturated ($C_7$ to $C_{15}$) hydrocarbon chain can be an alkyl, an alkenyl, or an alkynyl group. In some embodiments, the group is a $C_{12}$ alkyl or a $C_{12}$ alkylene. In one embodiment, R is $C_{12}H_{25}$.

The acyl, ester, carboxylic acid, or alkoxy groups can be substituted or unsubstituted. Suitable substituents include, for example, halogens, hydroxyl, amino, amino alkyl, acyl, thioacyl, CN, SH, ester, thioester, alkoxy, aryloxy, and alkylthio.

In some embodiments, R is $C_{12}H_{25}$; $R^1$ is hydrogen, bromine, chlorine, CHO or COOH; Y is OH; and X is oxygen or sulfur. For example, the COBRA compounds of formula I can be:

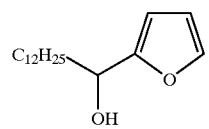

AC-6

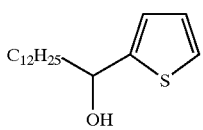

AC-10

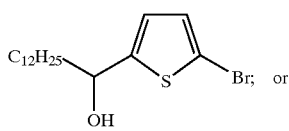

AC-11

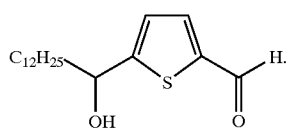

AC-12

In another aspect of the invention, COBRA compounds are provided of the general formula II:

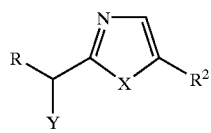

(II)

where

X is NH, O, or S;

R is a saturated or unsaturated ($C_7$ to $C_{15}$) hydrocarbon chain;

$R^2$ is hydrogen, OH, ($C_1$ to $C_6$) alkoxy, ($C_1$ to $C_6$) alkyl, ($C_1$ to $C_6$)alkenyl, ($C_1$ to $C_6$) alkynyl, ($C_3$ to $C_7$) cycloalkyl, aryl, heteroaryl, halogen, ($C_1$ to $C_6$) acyl, ($C_1$ to $C_6$) ester, or ($C_1$ to $C_6$) carboxylic acid;

Y is OH, SH, CN, halogen, or ($C_1$ to $C_6$) alkoxy; and pharmaceutically acceptable salt thereof.

The saturated or unsaturated ($C_7$ to $C_{15}$) hydrocarbon chain can be an alkyl, an alkenyl, or an alkynyl group. In some embodiments, the group is a $C_{12}$ alkyl or a $C_{12}$ alkylene. In one embodiment, R is $C_{12}H_{25}$.

The alkyl, alkenyl, alkynyl, cycloalkyl, aryl, heteroaryl, acyl, ester, carboxylic acid, and alkoxy groups can be substituted or unsubstituted. Suitable substituents include, for example, halogens, hydroxyl, amino, amino alkyl, acyl, thioacyl, CN, SH, ester, thioester, alkoxy, aryloxy, and alkylthio.

In some embodiments of formula II, R is $C_{12}H_{25}$; Y is OH; X is S or NH; and $R^2$ is hydrogen or a ($C_1$ to $C_6$) alkyl. For example, the COBRA compounds of formula II include

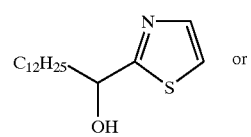

AC-13

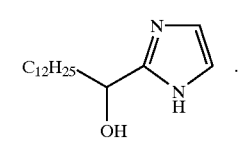

AC-14

In yet another aspect of the invention, the COBRA compound has the general formula III:

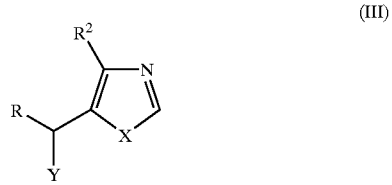

(III)

where

X is NH, O, or S;

R is a saturated or unsaturated ($C_7$ to $C_{15}$) hydrocarbon chain;

$R^2$ is hydrogen, OH, ($C_1$ to $C_6$) alkoxy, ($C_1$ to $C_6$) alkyl, ($C_1$ to $C_6$)alkenyl, ($C_1$ to $C_6$) alkynyl, ($C_3$ to $C_7$) cycloalkyl, aryl, heteroaryl, halogen, ($C_1$ to $C_6$) acyl, ($C_1$ to $C_6$) ester, or ($C_1$ to $C_6$) carboxylic acid;

Y is OH, SH, CN, halo, or ($C_1$ to $C_6$) alkoxy; and pharmaceutically acceptable salt thereof.

The saturated or unsaturated ($C_7$ to $C_{15}$) hydrocarbon chain can be an alkyl, an alkenyl, or an alkynyl group. In some embodiments, the group is a $C_{12}$ alkyl or a $C_{12}$ alkylene. In one embodiment, R is $C_{12}H_{25}$.

The alkyl, alkenyl, alkynyl, cycloalkyl, aryl, heteroaryl, acyl, ester, carboxylic acid, and alkoxy groups can be substituted or unsubstituted. Suitable substituents include, for example, halogens, hydroxyl, amino, amino alkyl, acyl, thioacyl, CN, SH, ester, thioester, alkoxy, aryloxy, and alkylthio.

In some embodiments of formula III, R is $C_{12}H_{25}$; Y is OH; X is S or NH; and $R^2$ is hydrogen or a ($C_1$ to $C_6$) alkyl. For example, the COBRA compounds of formula II include

AC-15

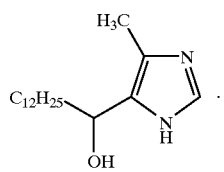

Salts

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms can be regenerated by treating the salt form with a base. For example, dilute solutions of aqueous base can be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

Depolymerization of Tubulin

The compounds of the invention bind to tubulin at the COBRA binding pocket of tubulin. On binding of the tubulin binding compounds, tubulin is caused to depolymerize and/or inhibition of tubulin assembly results. Suitable assays for the anti-tubulin acitivity of the inventive compounds are disclosed in the Examples below.

Treatment of Proliferative Disorders

The compounds of the invention are useful to inhibit cell division and proliferation of non-cancerous cells. According to the method of the inveniton, disorders associated with cell proliferation are treated by administration of the compounds and compositions of the invention.

Such disorders include, for example, EBV-induced lymphoproliferative disease and lymphoma; neointimal hypoplasia, for example in patients with athlerosclerosis and patients undergoing balloon angioplasty; proliferative effects secondary to diabetes, including vascular proliferation and retinopathy; psoriasis; benign tumors, including angiomas, fiberomas, and myomas, histiocytosis, osteoporosis, mastocytosis, and myeleoproliferative disorders such as polycytemiavera.

Tumor Treatment

The compounds of the invention are effective cytotoxic agents, for example, against tumor cells such as leukemia cells. In the methods of the invention, the cytotoxic effects are achieved by contacting cells, such as tumor cells, with micromolar amounts of the inhibitory compound.

The compounds of the invention can be used in methods of tumor treatment, for example, administering to a subject a compound of the invention in order to achieve an inhibition of tumor cell tubulin assembly and/or depolymerization of tumor cell tubulin, inhibition of tumor cell growth, a killing of tumor cells, induced apoptosis, and/or increased patient survival time.

The anti-cancer tubulin binding compounds of the invention are suitable for use in mammals. As used herein, "mammals" means any class of higher vertebrates that nourish their young with milk secreted by mammary glands, including, for example, humans, rabbits, and monkeys.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and can be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents, and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds can be administered directly to a tumor by tumor injection. In another embodiment of the invention, the compounds can be administered using systemic delivery by intravenous injection.

Solutions or suspensions of the compounds can be prepared in water, isotonic saline (PBS), and optionally mixed with a nontoxic surfactant. Dispersions can also be prepared in glycerol, liquid polyethylene, glycols, DNA, vegetable oils, triacetin and mixtures thereof. Under ordinary conditions of storage and use, these preparations can contain a preservative to prevent the growth of microorganisms.

The pharmaceutical dosage form suitable for injection or infusion use can include sterile, aqueous solutions, dispersions, or sterile powders comprising an active ingredient which are adapted for the extemporaneous preparation of sterile injectable or infusible solutions or dispersions. The final dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols, and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption such as, for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" refers to a complex formed with two or more compounds.

The phrase "targeting moiety" refers to a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When used in vivo to kill or inhibit the growth of tumor cells, the administered dose is that amount that can produce the desired effect, such as the amount sufficient to reduce or eliminate tumors. Appropriate amounts can be determined by those skilled in the art, extrapolating using known methods and relationships, from the in vitro data provided in the Examples.

In general, the dose of the COBRA tubulin binding compounds effective to achieve tumor cell apoptosis, reduction in tumors, and increased survival time, is 1–100 mg/kg body weight/dose for a direct targeted administration. The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less can be useful.

In addition, the compositions of the invention can be administered in combination with other anti-tumor therapies. In such combination therapy, the administered dose of the tubulin binding compounds can be less than for single drug therapy.

All publications, patents, and patent documents described herein are incorporated by reference as if fully set forth. The invention described herein can be modified to include alternative embodiments. All such obvious alternatives are within the spirit and scope of the invention, as claimed below.

EXAMPLES

The invention can be further clarified by reference to the following Examples, which serve to exemplify some of the embodiments, and not to limit the invention in any way.

Chemistry Methods

All chemicals were purchased from Aldrich (Milwaukee, Wis.) and were used without further purification. Unless otherwise noted, each reaction vessel was secured with a rubber septa, and the reaction was performed under nitrogen atmosphere. $^1H$ and $^{13}C$ NMR spectra were obtained on a Varian Mercury 300 instrument at ambient temperature in the solvent specified. Melting points were determined using a Fisher-Johns melting point apparatus and are uncorrected. FT-IR spectra were recorded on a Nicolet Protege 460 spectrometer. GC/MS was obtained on a HP 6890 GC System equipped with a HP 5973 Mass Selective Detector.

Example 1

Reaction Schemes for Synthesis of AC-4

The tubulin depolymerizing COBRA compounds were quickly synthesized in one step from commercially available starting materials. For example, AC-4 was prepared by reacting dodecylmagnesium chloride 1 and 5-(hydroxymethyl)furfural 2 (Scheme 1). AC-4 was synthesized by modification of the first generation of COBRA compounds, namely COBRA-1 and COBRA-2 disclosed in U.S. Pat. No. 6,258,841 B1. Compared with the synthesis of COBRA-1 and COBRA-2, the synthesis of AC-4 (Scheme 1) was dramatically simplified by replacing the chiral THF moiety in COBRA-1 and COBRA-2 with the achiral furan moiety in AC-4.

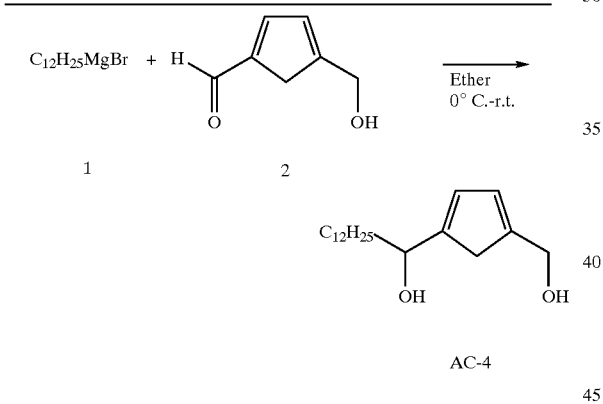

Dodecylmagnesium chloride (25 mL of 1M solution in ether) was added to the solution of 5-(hydroxymethyl) furfural (1.26 g, 10.0 mmol) in anhydrous ether (15 mL) at 0° C. The reaction mixture was stirred at room temperature for 3 h and then quenched with saturated ammonium chloride. The mixture was partitioned between ether (120 mL) and water (30 mL). The organic phase was washed with brine, dried over anhydrous $MgSO_4$, filtered and concentrated. Flash column chromatography furnished compound AC-4 as a white solid (2.58 g, 87%).

Melting point 56–57° C.; $^1$H NMR (300 MHz, $CDCl_3$) δ 6.14 (d, J=3.5 Hz, 1H), 6.09 (d, J=3.5 Hz, 1H, 4.55 (t, J=7.0 Hz, 1H), 4.46 (s, 2H), 3.22 (bs, 1H), 3.06 (bs, 1H), 1.77 (m, 2H), 1.41–1.20 (m, 20H), 0.85 (t, J=6.5 Hz, 3H); $^{13}$C NMR ($CDCl_3$) δ 156.65, 153.10, 108.13, 106.33, 67.56, 57.12, 35.28, 31.96, 29.73, 29.71, 29.67, 29.62, 29.48, 29.41, 25.70, 22.75, 14.19; IR (neat) 3195, 2922, 2845, 1468, 1014 $cm^{-1}$.

Example 2

Synthesis and Characterization of AC-4 Analogs

A series of AC-4 analogs were synthesized.

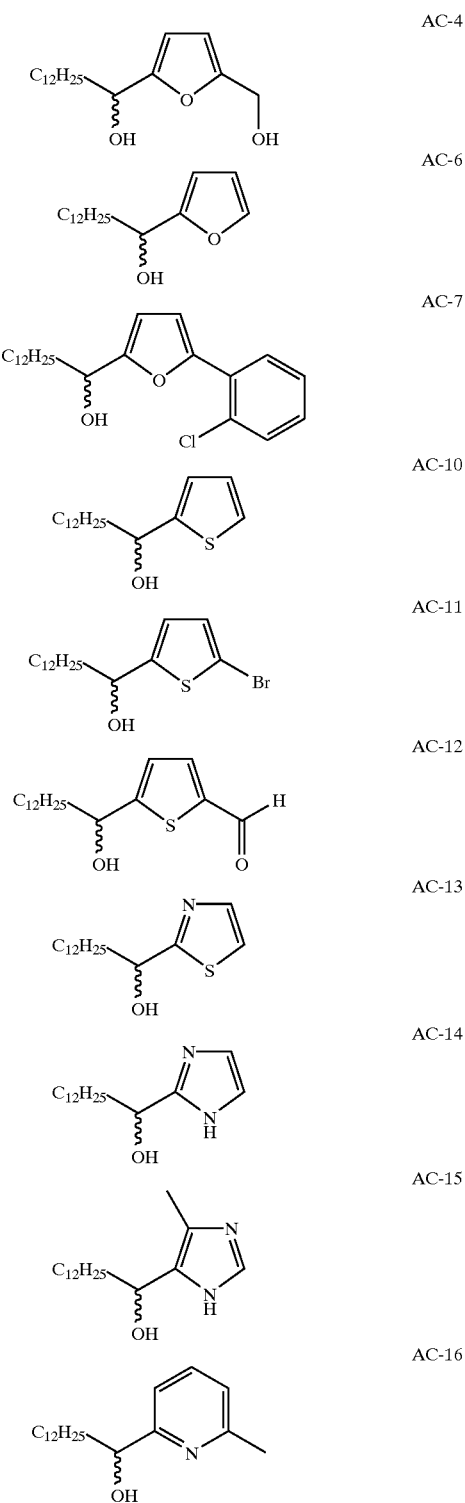

-continued

AC-17

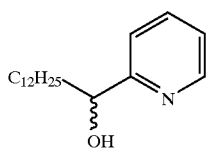

Using Quest 205 Organic Synthesizer (Argonaut Technologies, San Carlos, Calif.), compounds AC-6, AC-7, AC-10, AC-11, AC-12, AC-13, AC-15, AC-16 and AC-17 were synthesized in a parallel fashion to AC-4 by reacting dodecylmagnesium chloride 1 with the corresponding aldehydes under the same conditions as shown in Scheme 1.

AC-14 was synthesized by refluxing 2-imidazolecarboxaldehyde 3 and dodecylmagnesium chloride 1 in THF (Scheme 2) since 1 and 3 did not react under the low temperature conditions used in Scheme 1.

Scheme 2

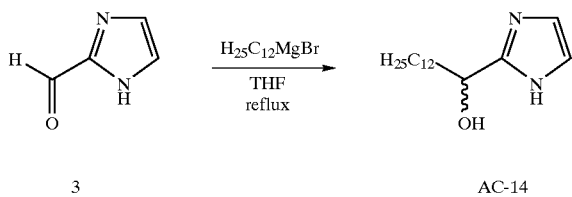

AC-12 was synthesized by reacting 2,5-thiophene dicarboxaldehyde 4 with dodecylmagnesium chloride 1 (Scheme 3).

Scheme 3
Synthesis of AC-12.

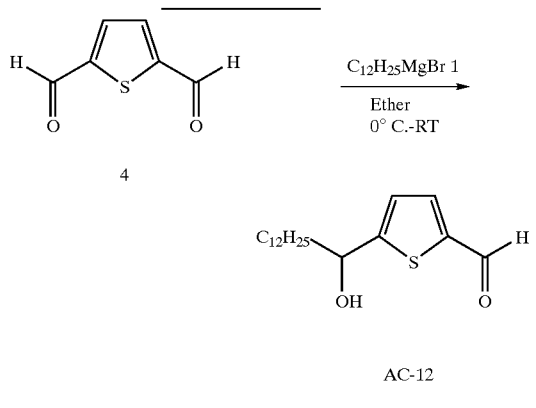

AC-6

AC-6 was synthesized by following the method described for the synthesis of AC-4.

Melting point: 40–41° C. $^1$H NMR (300 MHz, CDCl$_3$) δ 7.35 (m, 1H), 6.31 (m, 1H), 6.21 (m, 1H), 4.65 (m, 1H), 1.83 (m, 3H), 1.30 (m, 20H), 0.86 (t, J=6.5 Hz, 3H); $^{13}$C NMR (75 MHz, CDCl$_3$) δ 156.73, 141.73, 110.02, 105.69, 67.85, 35.61, 31.99, 29.74, 29.72, 29.65, 29.60, 29.47, 29.43, 25.62, 22.78, 14.24; IR (neat) 3350, 2916, 2848, 1457, 725 cm$^{-1}$.

AC-7

AC-7 was an orange waxy liquid; synthesized by following the method described for the synthesis of AC-4.

$^1$H NMR (300 MHz, CDCl$_3$) δ 7.83 (dd, J=8.0, 1.5 Hz, 1H), 7.41 (dd, J=8.0, 1.5 Hz, 1H), 7.29 (ddd, J=8.0, 8.0, 1.5 Hz, 1H), 7.16 (ddd, J=8.0, 8.0, 1.5 Hz, 1H), 7.05 (d, J=3.0 Hz, 1H), 6.35 (d, J=3.0 Hz, 1H), 4.71 (m, 1H), 2.03 (d, J=3.5 Hz, 1H), 1.89 (m, 2H), 1.49–1.24 (m, 20H), 0.87 (t, J=6.5 Hz, 3H); $^{13}$C NMR (75 MHz, CDCl$_3$) δ 156.42, 149.26, 130.56, 129.87, 128.98, 127.83, 127.66, 126.69, 111.46, 107.87, 67.92, 35.70, 31.98, 29.74, 29.71, 29.65, 29.60, 29.48, 29.43, 25.61, 22.77, 14.23; IR (neat) 3346, 2924, 2854, 1471, 1022, 754 cm$^{-1}$.

AC-10

AC-10 was a brown liquid, synthesized by following the method described for the synthesis of AC-4.

$^1$H NMR (300 MHz, CDCl$_3$) δ 7.24 (m, 1H), 6.95 (m, 2H), 4.90 (t, J=6.5 Hz, 1H), 2.01 (s, 1H), 1.82 (m, 2H), 1.43 (m,1H), 1.23 (m, 19H), 0.86 (t, J=6.5 Hz, 3H); $^{13}$C NMR (75 MHz, CDCl$_3$) δ 148.81, 126.45, 124.34, 123.57, 70.36, 39.36, 31.98, 29.73, 29.70, 29.64, 29.59, 29.45, 29.42, 25.86, 22.77, 14.22; IR (neat) 3354, 2924, 2854, 2361, 1466, 696 cm$^{-1}$.

AC-11

AC-11 was a yellowish wax, synthesized by following the method described for the synthesis of AC-4.

$^1$H NMR (300 MHz, CDCl$_3$) δ 6.87 (d, J=4.0 Hz, 1H), 6.68 (d, J=4.0 Hz, 1H), 4.79 (t, J=6.5 Hz, 1H), 2.01 (bs, 1H), 1.77(m, 2H), 1.45–1.16 (m, 20H), 0.86 (t, J=6.5, 3H); $^{13}$C NMR(75 MHz, CDCl$_3$) δ 150.45, 129.18, 123.84, 111.22, 70.59, 39.13, 31.99, 29.73, 29.71, 29.68, 29.57, 29.43, 29.40, 25.70, 22.78, 14.24; IR (neat) 3334, 2924, 2852, 1466, 1444, 968, 795 cm$^{-1}$.

AC-12

Using the ratio of 2,5-thiophene dicarboxaldehyde 4: dodecylmagnesium chloride 1=1:1, AC-12 was synthesized by following the conditions described in the synthesis of AC-4.

$^1$H NMR (300 MHz, CDCl$_3$) δ 9.62 (s, 1H); 7.01 (d, J=4.0 Hz, 1H); 6.61 (t, J=4.0 Hz, 1H); 4.44 (m, 1H), 1.55 (m, 2H), 1.37–1.20 (m, 21H); 0.93 (t, J=6.5 Hz, 3H); $^{13}$C NMR (75 MHz, CDCl$_3$) δ 182.80, 160.09, 142.17, 136.37, 124.30, 70.55, 39.41, 31.98, 29.71, 29.70, 29.68, 29.61, 29.55, 29.41, 29.39, 25.50, 22.77, 14.22; IR (neat) 3417, 2924, 2854, 1668, 1460 cm$^{-1}$.

AC-13

AC-13 was synthesized by following the method described for the synthesis of AC-4.

Melting point: 60–61° C.; $^1$H NMR (300 MHz, CDCl$_3$) δ 7.68 (d, J=3.5 Hz, 1H), 7.26 (d, J=3.5 Hz, 1H), 4.97 (m, 1H), 3.23 (d, J=4.5, 1H), 1.98–1.77 (m, 2H), 1.50–1.37 (m, 2H), 1.23 (bs, 18H), 0.86 (t, J=6.5 Hz, 3H); $^{13}$C NMR (75 MHz, CDCl$_3$) δ 175.24, 141.97, 118.71, 71.91, 38.38, 31.98, 29.73, 29.70, 29.63, 29.56, 29.45, 29.42, 25.25, 22.77, 14.22; IR (neat) 3236, 2914, 2848 1470, 743 cm$^{-1}$.

AC-14

AC-14 was synthesized by following the method described for the synthesis of AC-4).

Melting point: 97–98° C.; $^1$H NMR (300 MHz, CD$_3$OD) δ 6.98 (s, 2H), 4.74 (t, J=6.5, 1H), 1.85 (m, 2H), 1.31 (bs, 20H), 0.93 (t, J=6.5 Hz, 3H); $^{13}$C NMR (75 MHz, CD$_3$OD) δ 153.02, 122.97, 69.86, 38.72, 33.98, 31.69, 31.65, 31.58, 31.38, 27.22, 24.65, 15.37; IR (neat) 3163, 3078, 2916, 2848, 1468 cm$^{-1}$.

AC-15

AC-15 was synthesized by following the method described for the synthesis of AC-4.

Melting point: 0.300° C., $^1$H NMR (300 MHz, CD$_3$OD) δ 7.49 (s, 1H), 5.04 (bs, 2H), 4.70 (t J=7.0 Hz, 1H), 2.24 (s, 3H), 1.86 (m, 2H), 1.31 (m, 20H), 0.93 (t, J=6.5 Hz, 3H); $^{13}$C NMR (75 MHz, CD$_3$OD) δ 135.19, 68.01, 38.74, 34.01, 31.76, 31.73, 31.70, 31.66, 31.65, 31.51, 31.43, 27.85, 24.69, 15.45, 11.74; IR (neat) cm$^{-1}$.

AC-16

AC-16 was synthesized by following the method described for the synthesis of AC-4.

Melting point: 50–52° C.; $^1$H NMR (300 MHz, CD$_3$OD) δ 7.53 (dd, J=7.5, 7.5 Hz, 1H), 7.01 (d, J=7.5 Hz, 1H), 7.00 (d, J=7.5 Hz), 4.66 (dd, J=4.0, 8.0 Hz, 1H), 4.46 (bs, 1H), 2.52 (s,3H), 1.76 (m, 1H), 1.63 (m, 1H), 1.40 (m, 2H), 1.22 (m,18H), 0.86 (t, J=6.5 Hz, 3H); $^{13}$C NMR (75 MHz, CD$_3$OD) δ 161.12, 156.73, 136.71, 121.48, 117.04, 72.30, 38.80, 31.99, 29.73, 29.69, 29.66, 29.43, 25.41, 24.34, 22.78, 14.24; IR (neat) 3244, 2922, 2850, 2361 cm$^{-1}$.

AC-17

AC-17 was synthesized by following the method described for the synthesis of AC-4.

Melting point: 49–50° C.; $^1$H NMR (300 MHz, CD$_3$OD) δ 8.50 (d, J=5.0 Hz, 1H), 7.64 (ddd, J=7.5, 7.5, 1.5 Hz, 1H), 7.23 (d, J=7.8 Hz, 1H), 7.16 (ddd, J=7.2, 5.0, 0.9 Hz, 1H), 4.70 (dd, J=4.5, 7.5 Hz, 1H), 4.20 (bs, 1H), 1.77 (m, 1H), 1.66 (m, 1H), 1.38 (m, 2H), 1.22 (bs, 18H), 0.85 (t, J=6.5 Hz, 3H); $^{13}$C NMR (75 MHz, CD$_3$OD) δ 162.17, 147.98, 136.44, 122.06, 120.20, 72.77, 38.69, 31.97, 29.72, 29.70, 29.68, 29.66, 29.63, 29.41, 25.35, 22.76, 14.21; IR (neat) 3385, 2924, 2854, 1595, 1468, 1047 cm$^{-1}$.

Example 3

Anti-Cancer Activity of COBRA Compounds as Measured by MTT Assays

The following human cancer cell lines were used in the present study: human leukemic cell lines Molt-3 and NALM-6. These cell lines were obtained from American Type Culture Collection (Manassas, Va.) and maintained as continuous cell lines in Dulbecco's modified Eagles's medium supplemented with 10% fetal bovine serum and antibiotics.

The antiproliferative activity of the COBRA compounds was examined against a panel of 2 different human tumor cell lines using standard MTT (3-[4,5-dimethylthiazol-2-yl]-2,5-diphenyl tetrazolium bromide) assays (Narla, R. K., Liu, X. P., Klis, D. and Uckun, F. M., Clin. Cancer Res., 1998, 4, 2463), (Boehringer Mannheim Corp., Indianapolis, Ind.). Briefly, exponentially growing brain tumor cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the test compounds at concentrations ranging from 1.0 to 250 µM. Triplicate wells were used for each treatment. The cells were incubated with the various compounds for 24–36 hours at 37° C. in a humidified 5% CO$_2$ atmosphere. To each well, 10 µl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm. To translate the OD $_{540}$ values into the number of live cells in each well, the OD $_{540}$ values were compared to those on standard OD $_{540}$—versus—cell number curves generated for each cell line. The percent survival was calculated using the formula: survival=Live cell number[test]×100/Live cell number [control].

IC$_{50}$ values were calculated by non-linear regression analysis using an Graphpad Prism software version 2.0 (Graphpad Software, Inc., San Diego, Calif.).

TABLE 1

Anti-Cancer Activity COBRA Compound

| Compound | MOLT-3 Lymphoma IC$_{50}$ (µM) | NALM-6 Leukemia IC$_{50}$ (µM) |
| --- | --- | --- |
| AC-6 | >250 | 229 |
| AC-7 | >250 | >250 |
| AC-10 | 125 | 204 |
| AC-11 | 2 | 4 |
| AC-12 | 33 | 6 |
| AC-13 | 4 | >250 |
| AC-14 | 58 | 3 |
| AC-15 | 9 | 25 |
| AC-16 | >250 | 236 |
| AC-17 | 246 | 221 |

All publications, patents, and patent documents described herein are incorporated by reference as if fully set forth. The invention described herein can be modified to include alternative embodiments. All such obvious alternatives are within the spirit and scope of the invention, as claimed below.

We claim:

1. A compound of formula I:

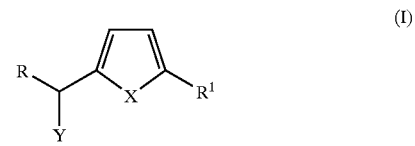

wherein

X is S;

R is a saturated or unsaturated C$_{12}$ hydrocarbon chain;

R$^1$ is hydrogen, halogen, OH, (C$_1$ to C$_6$) alkoxy, (C$_1$ to C$_6$) acyl, (C$_1$ to C$_6$) ester, or (C$_1$ to C$_6$) carboxylic acid;

Y is OH, SH, CN, halogen, or (C$_1$ to C$_6$) alkoxy; and pharmaceutically acceptable salts thereof.

2. The compound of claim 1, wherein R is a C$_{12}$ alkyl or a C$_{12}$ alkylene.

3. The compound of claim 1, wherein R is C$_{12}$H$_{25}$; R$^1$ is hydrogen, bromine, CHO, or COOH; Y is OH.

4. The compound of claim 1, having the formula

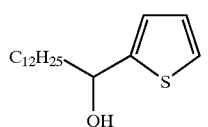.

5. The compound of claim 1, having the formula

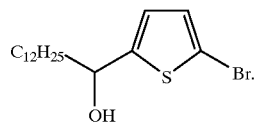

6. The compound of claim 1, having the formula

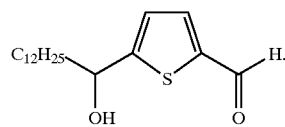

7. A composition comprising the compound of claim 1 and a pharmaceutically acceptable carrier or diluent.

8. The composition of claim 7, wherein the compound is

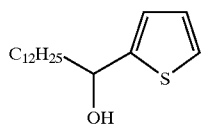.

9. The composition of claim 7, wherein the compound is

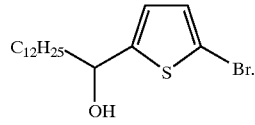

10. The composition of claim 7, wherein the compound is

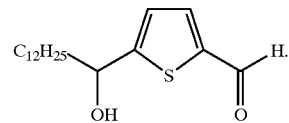

11. A method for inhibiting the proliferation of tumor cells comprising administering to said tumor cells an inhibitory amount of the compound of claim 1.

12. A method for treating cancer in a patient comprising administering to said patient a therapeutically effective amount of a compound of claim 1.

13. The method of claim 12, wherein the cancer is leukemia.

14. A method for inducing cytotoxicity in a cell comprising administering to said cell a cytotoxic dose of a compound of claim 1.

15. The method of claim 14, wherein the compound is

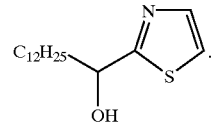.

16. A The method of claim 14, wherein the compound is

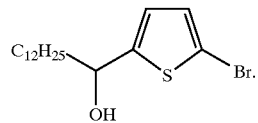

17. The method of claim 14, wherein the compound is

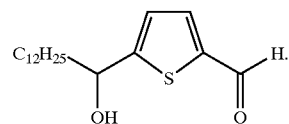

* * * * *

UNITED STATES PATENT AND TRADEMARK OFFICE
CERTIFICATE OF CORRECTION

PATENT NO.    : 6,734,207 B2
DATED         : May 11, 2004
INVENTOR(S)   : Uckun et al.

It is certified that error appears in the above-identified patent and that said Letters Patent is hereby corrected as shown below:

Column 18,
Line 22, the molecule is incorrect. The molecule should read

-- 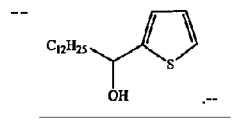 --

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,734,207 B2
DATED : May 11, 2004
INVENTOR(S) : Uckun et al.

It is certified that error appears in the above-identified patent and that said Letters Patent is hereby corrected as shown below:

Title page,
Item [56], References Cited, OTHER PUBLICATIONS, add the following cited reference:
-- Bai, R. et al., (August 1, 1995), *Biochemistry*, 34(30):9714-9721, "The Spongistarins, Potently Cytotoxic Inhibitors of Tubulin Polymerization, Bind in a Distinct Region of the Vinca Domain". --

Signed and Sealed this

Twelfth Day of April, 2005

JON W. DUDAS
*Director of the United States Patent and Trademark Office*